(12) United States Patent
Neculaes et al.

(10) Patent No.: US 10,383,915 B2
(45) Date of Patent: Aug. 20, 2019

(54) PLATELET ACTIVATION AND GROWTH FACTOR RELEASE USING ELECTRIC PULSES

(71) Applicant: GENERAL ELECTRIC COMPANY, Schenectady, NY (US)

(72) Inventors: Vasile Bogdan Neculaes, Niskayuna, NY (US); Andrew Soliz Torres, Niskayuna, NY (US); Antonio Caiafa, Albany, NY (US); Brian Dun-Lan Lee, Rexford, NY (US); Allen Lawrence Garner, West Layfayette, IN (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 29 days.

(21) Appl. No.: 15/251,990

(22) Filed: Aug. 30, 2016

(65) Prior Publication Data
US 2016/0367632 A1   Dec. 22, 2016

Related U.S. Application Data

(62) Division of application No. 14/157,819, filed on Jan. 17, 2014, now Pat. No. 9,452,199.

(51) Int. Cl.
| | | |
|---|---|---|
| *G01N 27/00* | (2006.01) | |
| *A61K 38/18* | (2006.01) | |
| *A61K 35/19* | (2015.01) | |
| *G01N 33/49* | (2006.01) | |
| *C12N 13/00* | (2006.01) | |
| *G01N 33/487* | (2006.01) | |

(52) U.S. Cl.
CPC .......... *A61K 38/1858* (2013.01); *A61K 35/19* (2013.01); *C12N 13/00* (2013.01); *G01N 33/48707* (2013.01); *G01N 33/49* (2013.01)

(58) Field of Classification Search
CPC ....................................................... G01N 27/00
USPC ................................ 422/82.01; 436/43, 174
See application file for complete search history.

(56) References Cited

U.S. PATENT DOCUMENTS

| | | |
|---|---|---|
| 6,326,177 B1 | 12/2001 | Schoenbach et al. |
| 6,897,069 B1 | 5/2005 | Jarvis et al. |
| 7,053,063 B2 | 5/2006 | Rubinsky et al. |
| 7,565,201 B2 | 7/2009 | Blackmore et al. |
| 7,750,605 B2 | 7/2010 | Ragsdale |

(Continued)

FOREIGN PATENT DOCUMENTS

| | | |
|---|---|---|
| CN | 1368886 A | 9/2002 |
| CN | 102548614 A | 7/2012 |

(Continued)

OTHER PUBLICATIONS

Freitag, Julian et al.; "Photoactivated platelet-rich plasma therapy for a traumatic knee chondral lesion", BMJ Case Reports 2012: doi 10.1136/bcr-2012-006858 (abstract only).

(Continued)

*Primary Examiner* — Brian J. Sines
(74) *Attorney, Agent, or Firm* — Fletcher Yoder, P.C.

(57) ABSTRACT

Methods and systems for releasing growth factors are disclosed. In certain embodiments, a blood sample is exposed to a sequence of one or more electric pulses to trigger release of a growth factor in the sample. In certain embodiments, the growth factor release is not accompanied by clotting within the blood sample.

11 Claims, 5 Drawing Sheets

(56) References Cited

U.S. PATENT DOCUMENTS

| | | | |
|---|---|---|---|
| 7,923,238 | B2 | 4/2011 | Ragsdale |
| 8,173,416 | B2 | 5/2012 | Muller-Hartmann et al. |
| 8,222,909 | B2 | 7/2012 | Ragsdale |
| 9,011,929 | B2 | 4/2015 | Park et al. |
| 2006/0269531 | A1 | 11/2006 | Beebe et al. |
| 2009/0023131 | A1 | 1/2009 | Muller-Hartmann et al. |
| 2012/0058500 | A1* | 3/2012 | Mitchell ............ B01L 3/502746 435/13 |
| 2013/0028880 | A1* | 1/2013 | Chen ..................... A61K 38/46 424/94.6 |
| 2014/0106430 | A1 | 4/2014 | Hargrave et al. |
| 2015/0202264 | A1* | 7/2015 | Neculaes ............... C12N 13/00 514/8.2 |

FOREIGN PATENT DOCUMENTS

| | | |
|---|---|---|
| WO | 2011/075614 A2 | 6/2011 |
| WO | 2012/125899 A1 | 9/2012 |

OTHER PUBLICATIONS

AdiStem PhotoActivated PRP & Stem Cell Technology website downloaded Jan. 17, 2014: http://www.adistem.com/technology/prp/.

Xiao, S. et al., "Pulsed Power of Wound Healing", IEEE International Power Modulators and High Voltage conference, Proceedings of the 2008, Piscataway, NJ, USA, May 27, 2008, pp. 69-72.

PCT Search Report and Written Opinion from corresponding PCT Application No. PCT/US2015/010817 dated May 3, 2015.

Zhang, et al., "Nanosecond pulse electric field (nanopulse): A novel non-ligand agonist for platelet activation", Archives of Biochemistry and Biophysics, Academic Press, US, vol. 471, No. 2, Dec. 23, 2007, pp. 240-248.

First Office Action and Search issued in connection with corresponding CN Application No. 201580004722.7 dated Mar. 22, 2018.

Khine, Michelle, et al.; "Single-cell electroporation arrays with real-time monitoring and feedback control," Lab Chip 2007, 7, 457-462.

JP Application No. 2016-545972; Office Action dated Dec. 20, 2018; 8 pages, including translation.

RU Application No. 2016126427; Office Action, dated Oct. 26, 2018; 6 pages.

TW Application No. 104100402; Office Action, 7 pages.

\* cited by examiner

NOT CLOTTED    CLOTTED

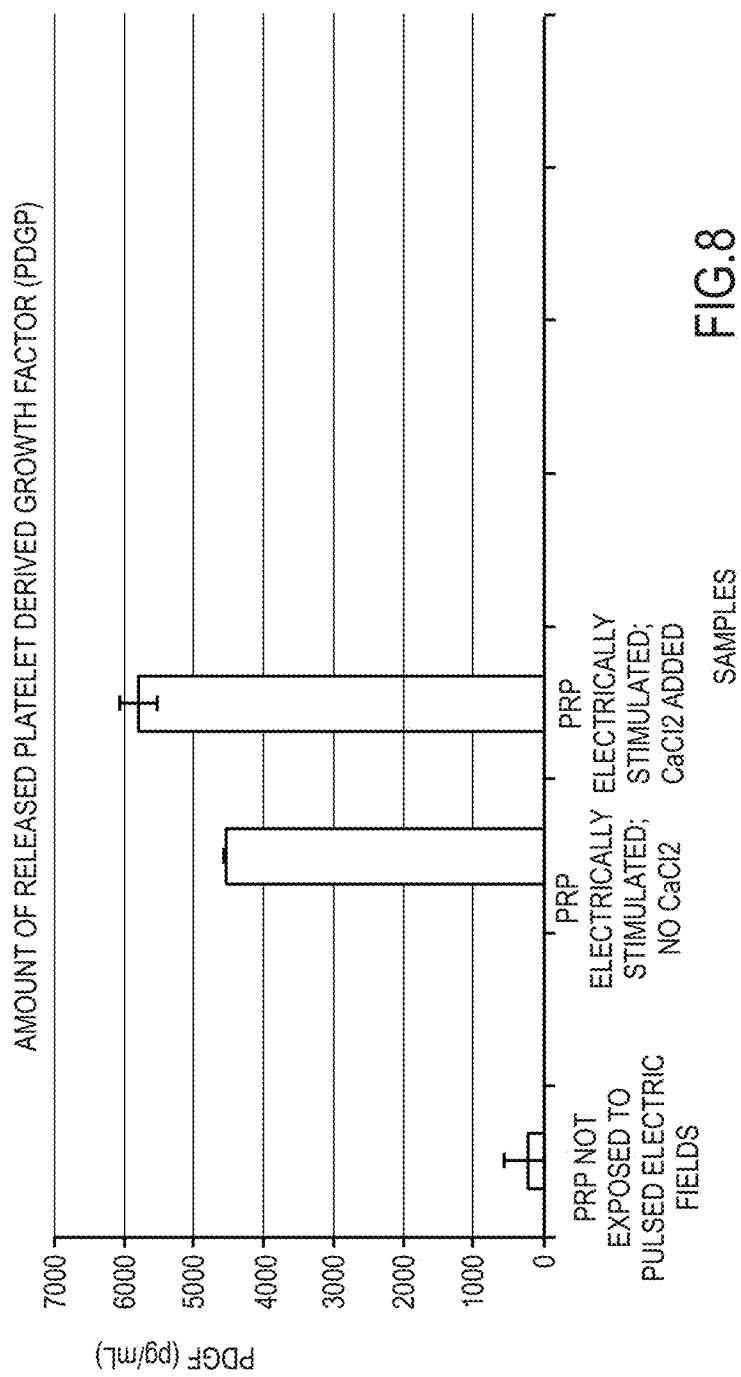

PLATELET ACTIVATION AND GROWTH FACTOR RELEASE USING ELECTRIC PULSES

CROSS-REFERENCE TO RELATED APPLICATION

This application claims priority to and the benefit of U.S. application Ser. No. 14/157,819, entitled "Platelet Activation and Growth Factor Release Using Electric Pulses", filed Jan. 17, 2014, and is related to U.S. application Ser. No. 15/252,032 (Applicant Matter No. 269575-14), entitled "Platelet Activation and Growth Factor Release Using Electric Pulses", filed Aug. 30, 2016, which are both herein incorporated by reference in their entirety for all purposes.

BACKGROUND

The subject matter disclosed herein relates generally to platelet therapy used in various medical applications, such as treatments for surgery or trauma. Specifically, the embodiments described relate to platelet activation and growth factor release in platelet rich plasma.

Platelet therapy is a wound healing treatment used for many types of injuries and conditions, such as nerve injuries, tendinitis, osteoarthritis, cardiac muscle injury, and bone repair and regeneration. Platelet therapy may also be used to speed up wound healing after surgery.

Generally, a doctor may draw blood from a patient; the blood is then centrifuged to generate platelet rich plasma (PRP). For in vivo platelet activation, the doctor may apply the PRP to the site without adding a platelet activator. Platelet activation, which includes growth factor release and clotting, is usually induced by the collagen within connective tissue. For ex vivo platelet activation, the doctor may trigger platelet activation within the PRP by adding a typical activator, such as thrombin, and then apply the activated PRP to the site.

For such ex vivo applications, bovine thrombin may be used to induce platelet activation. However, using animal-based thrombin may cause allergic reactions or possible contamination of the PRP with infectious agents. Alternatives to animal-based thrombin tend to be expensive and may still cause allergic reactions.

Further, there are some wound healing applications in which growth factor release is desired but the subsequent clotting is not. For example, a doctor may wish to inject a PRP sample with released growth factors into the site, which is a common treatment for joint injuries. Exposing a PRP sample to various types of light (e.g., infrared) may trigger growth factor release without the subsequent clotting. However, the experimental set-up is complex, which may be expensive and time-consuming to install in a laboratory. Additionally, the light exposure time for a sample may be long, which would subsequently increase the total time of the treatment.

BRIEF DESCRIPTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In a first embodiment, a method for inducing adenosine diphosphate (ADP) release in a blood sample includes exposing the blood sample to a current generated by a sensing circuit. One or more electrical properties of the blood sample are estimated based on the current. Based on the one or more electrical properties, a sequence of one or more electric pulses to be applied to the blood sample is parameterized. The blood sample is exposed to the sequence of one or more electric pulses to trigger a release of ADP in the blood sample. The release of ADP triggers platelet activation and clotting within the blood sample.

In a second embodiment, a method for releasing growth factors includes exposing a blood sample to a current generated by a sensing circuit. One or more electrical properties of the blood sample are estimated based on the current. Based on the one or more electrical properties, a sequence of one or more electric pulses to be applied to the blood sample is parameterized. The blood sample is exposed to the sequence of one or more electric pulses to trigger release of a growth factor in the blood sample. The growth factor release is not accompanied by clotting within the blood sample.

In a third embodiment, a method for treating a wound includes collecting a blood sample from a patient. The blood sample is exposed to a current generated by a sensing circuit. One or more electrical properties of the blood sample are estimated based on the current. Based on the one or more electrical properties, a sequence of one or more electric pulses to be applied to the blood sample is parameterized. The blood sample is then exposed to the sequence of one or more electric pulses to trigger release of a growth factor in the blood sample without accompanying clotting. The growth factor is then collected and used to treat the patient.

DRAWINGS

These and other features, aspects, and advantages of the present invention will become better understood when the following detailed description is read with reference to the accompanying drawings in which like characters represent like parts throughout the drawings, wherein:

FIG. 8 is a graph showing the amount of platelet derived growth factor (PDGF) released in the platelet rich plasma

DETAILED DESCRIPTION

Figure 1:
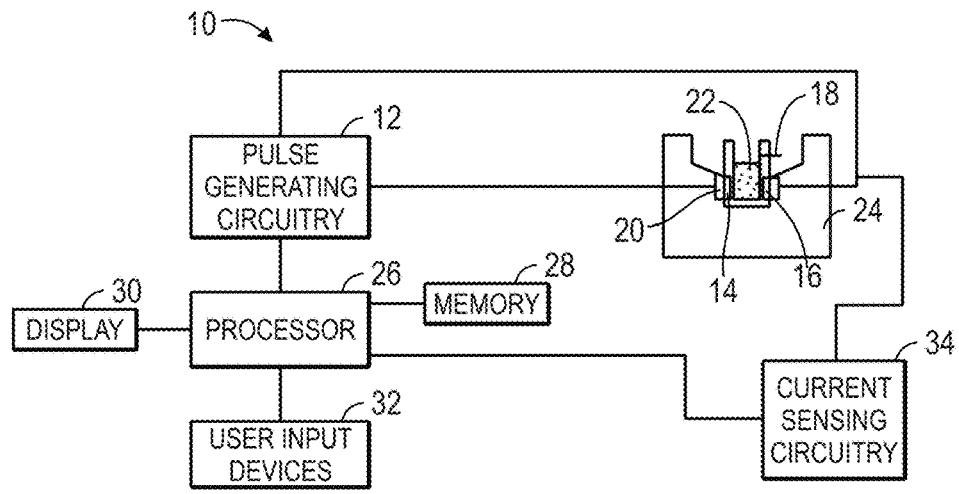
FIG. 1 is a schematic of a pulse generation system, in accordance with an embodiment of the present approach.

One or more specific embodiments of the present subject matter will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Platelet activation and/or aggregation may be used to treat wounds in vivo and/or ex vivo. During conventional processes, platelets in blood are exposed to a platelet activating compound, such as thrombin, which induces both the release of growth factors (e.g., platelet-derived growth factor (PDGF)) and clotting. For in vivo platelet activation, inactivated PRP is applied or injected at the site of injury. Typically, collagen within the connective tissue triggers platelet activation, growth factor release and clotting. For ex vivo platelet activation, a doctor may draw blood from a patient, and centrifuge the blood sample to produce a platelet rich plasma (PRP) sample. Calcium chloride ($CaCl_2$) and a platelet activating compound, such as thrombin, may be added to the PRP sample to trigger platelet activation and form a gel that is then applied to the wound. However, using animal-based thrombin in platelet activation may cause allergic reactions or possible contamination of the PRP sample. Further, alternatives to animal-based thrombin tend to be expensive, and may still cause allergic reactions.

Present embodiments relate to ex vivo platelet activation and growth factor release, including approaches for releasing growth factor without causing the clotting events typically associated with platelet activation. Specific wound healing applications may involve treating blood samples, including PRP samples, to release growth factors without clotting. Methods for ex vivo platelet activation discussed herein may include exposing a blood sample, such as a PRP sample, to electric pulses to trigger platelet activation. The release of adenosine diphosphate (ADP) may be observed as part of the platelet activation release in response to pulsed electric fields in certain implementations. The methods for ex vivo growth factor release may or may not involve chemicals being added to the blood sample prior to electrical stimulation, as discussed herein.

With the foregoing in mind, FIG. 1 shows schematically a pulse generation system 10 for ex vivo platelet activation and growth factor release. The system 10 may include pulse generating circuitry 12 and electrode sets (or arrays of electrodes) 14 and 16. In the depicted embodiment, the electrodes 14 and 16 are spaced apart on opposing sides of a cuvette 18. That is, the cuvette 18 is disposed between the electrodes and the electrodes 14 and 16 are coupled to the pulse generating circuitry via contacts 20. The cuvette 18 is configured to hold a sample 22 that contains platelets. In certain embodiments, the cuvette 18 may be disposable and removable from a sample holder 24 that includes the electrodes 14 and 16. Accordingly, insertion of the cuvette 18 and contact of the electrodes 14 and 16 with the contacts 20 allows the pulse generating circuitry to produce an electric pulse, and the sample 22 within the cuvette 18 is exposed to the pulses. As will be appreciated, the cuvette 18 is merely an example of a sample container, and any suitable container configured to hold the sample 22, contact the electrodes 14 and 16, and conduct the electric pulses may be used in conjunction with the system 10. The spacing between the electrodes 14 and 16 may influence the strength of the pulse's electric field, which is defined as the ratio of the applied voltage and the cuvette gap distance. For example, exposing a 1 cm wide cuvette to a 1 kV pulse yields a field strength of 1 kV/cm.

In certain embodiments, the system may include suitable control and input circuitry and may be implemented in a dedicated housing or may be coupled to a computer or other processor-based control system. The system 10 may include or communicate with a processor 26 that controls the pulse generating circuitry 12. Additional components of the system 10 may include a memory 28 storing instructions that are executed by the processor 26. Such instructions may include protocols and/or parameters for the electric pulses generated by the pulse generating circuitry 12. The processor 26 may include, for example, general-purpose single- or multi-chip microprocessors. In addition, the processor 26 may be any conventional special purpose processor, such as an application-specific processor or circuitry. The memory 28 may be any suitable non-transitory computer-readable medium such as a random access memory, mass storage device, a FLASH memory device, or removable memory. In addition, a display 30 may provide indications to an operator related to the operation of the system 10. The system 10 may include a user input device 32 (e.g., a keyboard, mouse, touchscreen, trackball, hand held device such as PDA or smart phone or any combination thereof) for activating the pulse generating circuitry 12 and/or selecting appropriate parameters.

The pulse generation system 10 as provided herein may be implemented as a single-purpose device for platelet activation or as a multi-purpose device that may be used for other electric field exposure applications, such as electroporation, in addition to platelet activation, as discussed herein. Further, the system 10 may be configured to generate an electric pulse according to one or more protocols. The protocols may be generated by user input and/or may be stored in the memory 28 to be selected by the user. In one embodiment, the pulse generating circuitry 12 may operate under control of the processor 26 to implement protocol that specifies predetermined electric field strength, pulse length, and/or total exposure time. Such a protocol may be determined by empirical or theoretical studies. In other embodiments, the system 10 may be configured to receive a user input related to the electric field strength, pulse length, and/or total exposure time, i.e., the user can specify one or more of these operational parameters. Further, the system 10 may be configured to generate a particular pulse shape or to generate a series of pulses that may differ from one another according to a user input and/or a stored protocol setting.

In certain embodiments, a pulse generated by the system 10 may have a duration from about 1 nanosecond to about 100 microseconds, and an electric field strength from about 0.1 kV/cm to about 350 kV/cm, depending on the application. As mentioned above, the electric field strength of the pulse is the applied voltage divided by the distance between the electrodes 14 and 16. While the pulses generated by the system 10 have an electric field strength of at least 0.1 kV/cm, they should not exceed the breakdown field of the suspension which includes the cells.

In some embodiments, the pulse generation system 10 may include sensing functionality. That is, the pulse generation system 10 may be configured to expose the sample 22 to a sensing signal, which may be an electric pulse with an electric field strength below that of the electric pulses used for platelet activation. The pulse generation system 10 may, as depicted in FIG. 1, include current sensing circuitry 34, which may acquire and/or process the sensing signal to estimate some of the electrical properties of the sample 22, including, but not limited to conductivity and permittivity. The current sensing circuitry 34 may be coupled to the processor 26, which may control the generation and processing of the sensing signal and, in some embodiments, may perform a portion of the processing. In other embodiments, the current sensing circuitry 34 may include a dedicated processor to control the processing of the sensing signal and may communicate with the processor 26 to report the results. Alternatively, the current sensing circuitry 34 may be integral with the pulse generating circuitry 12. In still other embodiments, the processing of the sensing signal may be performed by a dedicated processor as described above or the processor 26.

Figure 2:
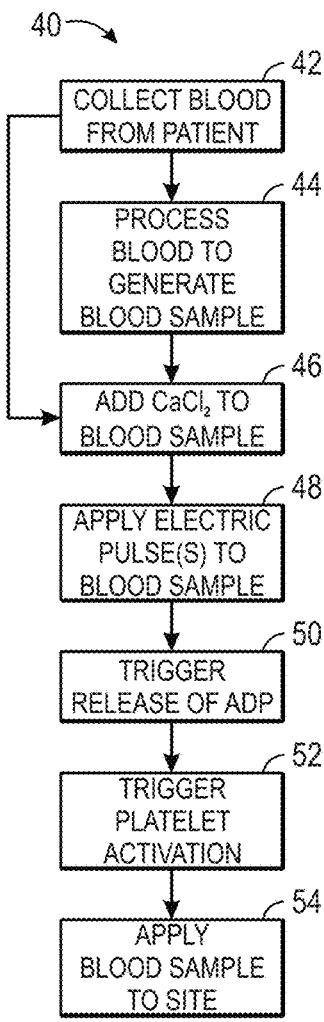
FIG. 2 is a flow chart illustrating a method for ex vivo platelet activation, in accordance with an embodiment of the present approach.

A method 40 for treating an injury using ex vivo platelet activation, as illustrated in FIG. 2, may be used in conjunction with the system 10. It should be understood that certain steps of the method 40 may be performed by an operator while other steps of the method may be performed by the system 10. At step 42, personnel (e.g., a doctor or nurse) draw blood from a patient. In certain embodiments, the drawn blood may be processed to generate a PRP sample in step 44. Various techniques suitable for platelet separation, such as centrifugation or filtration, may be used to generate the PRP sample. In such embodiments, the steps 46-54 may be performed using the PRP sample. Alternatively, step 44 may be skipped, and the remainder of the steps in the method 40 may be performed using a whole blood sample. In the depicted implementation, $CaCl_2$ is added to the sample in step 46, prior to exposure to one or more pulses via the system 10 during step 48. Adding $CaCl_2$ to the sample increases the likelihood and amount of calcium mobilization among the platelets, which facilitates platelet activation. The electrical stimulation of step 48 triggers the release of ADP within the sample in step 50 which then, in conjunction with the $CaCl_2$, triggers platelet activation in step 52. At step 54, the sample with activated platelets may then be applied to the site of injury on the patient.

As mentioned above, platelet activation is a process that in certain activation approaches involves both growth factor release and clotting. However, in certain situations, it may be desirable to avoid the clotting activity if possible. As discussed above, this may be accomplished using the pulsed electric fields as discussed herein.

Figure 3:
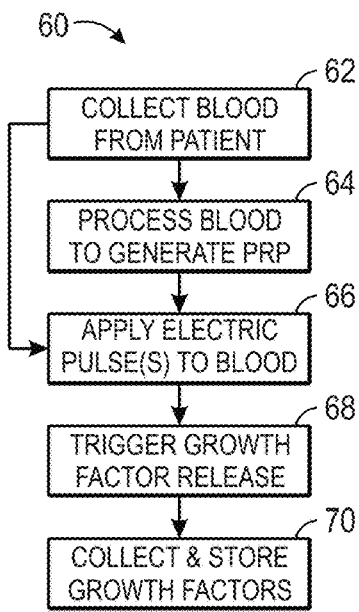
FIG. 3 is a flow chart illustrating a method for ex vivo growth factor release, in accordance with an embodiment of the present approach.

For example, turning to FIG. 3, a method 60 is described for triggering growth factor release without clotting. The method 60 uses electric pulses, similar to the platelet activation method 40, and as such, may be performed in part by the system 10. In step 62, personnel draw blood from a patient. In certain embodiments, the blood sample from step 62 may be processed to generate a PRP sample in step 64, as noted above. In other embodiments, as mentioned above, steps 66-70 of method 60 may be performed using a whole blood sample. At step 66, the sample is exposed to one or more pulses via the system 10, which triggers the release of growth factors in step 68. In this example, $CaCl_2$ is not added prior to or during exposure to the pulsed electrical fields. The released growth factors may then be collected and stored in step 70.

As described, the method 60 is similar to the method 40, with the exception of adding $CaCl_2$ to the sample prior to electrical stimulation. However, this distinction yields a different result in that, though growth factors are still released, no clotting occurs in the sample. As a result, the cuvette 18 contains only and any released growth factors after the execution of the protocol is executed.

Figure 4:
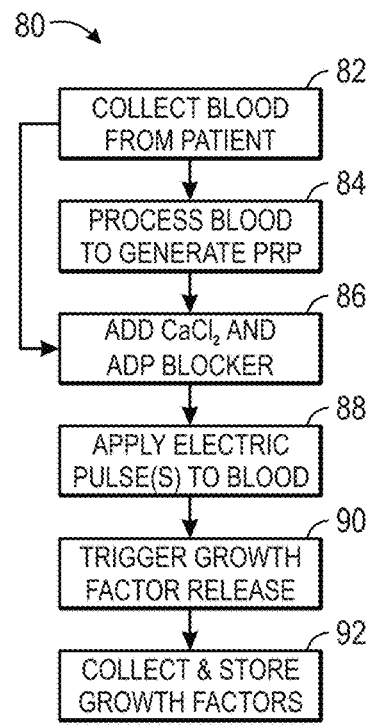
FIG. 4 is a flow chart illustrating a method of ex vivo growth factor release, in accordance with another embodiment of the present approach.

FIG. 4 illustrates an alternative method 80 for triggering growth factor release without clotting. Personnel draw blood from a patient in step 82, which may then be processed to generate a PRP sample in step 84. Alternately, steps 86-92 of method 80 may be performed using a whole blood sample. $CaCl_2$ and an ADP blocking chemical (e.g., apyrase) are then added to the sample in step 86. At step 88, the sample is exposed to one or more electric pulses via the system 10, which triggers the release of growth factors in step 90. The released growth factors are then collected and stored in step 92. In this example, the ADP blocking chemical acts to bind any ADP released due to the presence of the $CaCl_2$ in the sample, and no clotting is observed.

EXAMPLES

Figure 5:
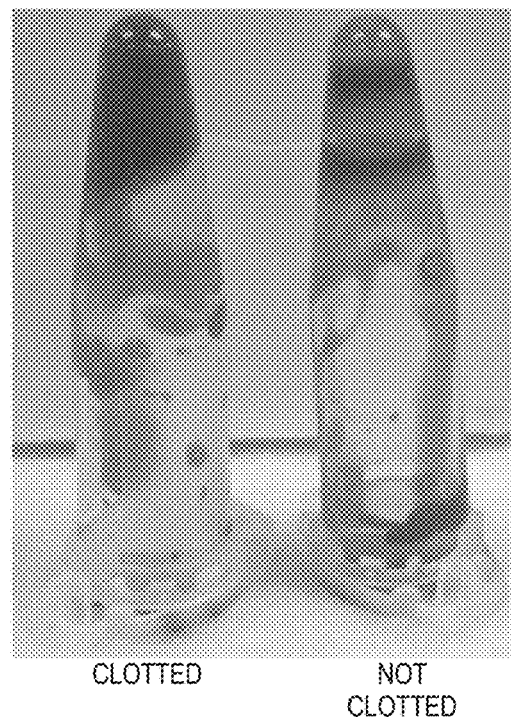
FIG. 5 illustrates a sample of platelet rich plasma activated using bovine thrombin (left hand side) and a sample of platelet rich plasma after exposure to electric pulses (right hand side) where growth factor release occurs without clotting.

Platelet Rich Plasma Samples with and without Calcium Chloride and ADP Blocker Addition Prior to Electrical Stimulation With the foregoing discussion in mind, FIG. 5 illustrates two samples of 3.7× concentration of platelet rich plasma (PRP). FIG. 5 illustrates a sample of platelet rich plasma activated using bovine thrombin (left hand side), where platelet activation is accompanied by growth factor release with clotting, as indicated by the PRP not flowing to the bottom of the tube. Conversely, shown on the right, a sample of platelet rich plasma after exposure to electric pulses (as discussed herein) is depicted where growth factor release occurs without clotting, as shown by PRP flowing to the bottom of the tube. Calcium chloride and apyrase, an adenosine diphosphate (ADP) blocking chemical, were added to the PRP sample in the tube on the right prior to electric pulse stimulation. Calcium chloride and apyrase were added prior to platelet activation using bovine thrombin in the sample on the left.

As illustrated, and as noted above, the sample activated using bovine thrombin generally remains at the tip of the tube, indicating that it has clotted. Thus, as may be understood from this study, ADP blocking does not affect the clotting cascade when thrombin is used for activation, thus resulting in clotting. Conversely, the sample on the right does not demonstrate the clotting observed in the other sample, and thus flows more freely toward the bottom of the tube. In view of these results, it is believed that the ADP blocking chemical acts to block the ADP released from the sample when exposed to both calcium chloride and the electrical pulses. With the ADP blocked, no clotting is observed even in the presence of $CaCl_2$. As depicted, this is a striking difference from the case where bovine thrombin is used, leading to the conclusion that ADP blocking does affect the clotting cascade when electrical stimulation is utilized. Thus, the sample on the right corresponds to a sample prepared in accordance with the method 80 of FIG. 4.

Figure 6:
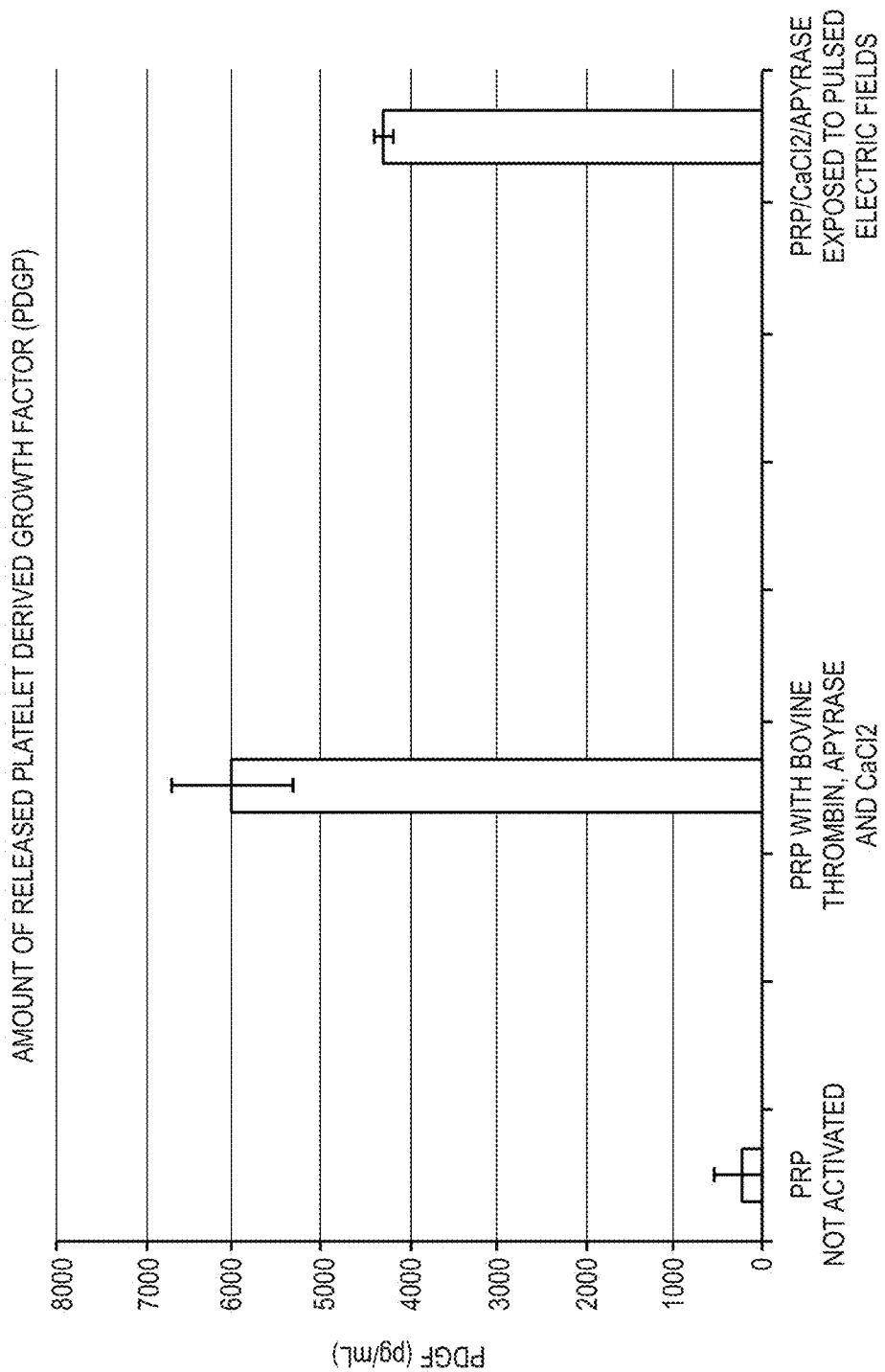
FIG. 6 is a graph showing the amount of platelet derived growth factor (PDGF) released in the platelet rich plasma samples illustrated in FIG. 5 using various approaches, including approaches discussed herein.

FIG. 6 compares the amount of platelet derived growth factor (PDGF) released for PRP samples that are not activated, PRP samples with calcium chloride and apyrase added and that are activated with bovine thrombin, and PRP samples with calcium chloride and apyrase added and that are exposed to electric pulses. Clotting occurs in the PRP sample activated with bovine thrombin, but does not occur in the PRP sample exposed to electric pulses. In particular, FIG. 6 is a graph showing the amount of platelet derived growth factor (PDGF) released in the platelet rich plasma samples illustrated in FIG. 5 using various approaches, including approaches discussed herein. As shown, pulsed electric fields can release growth factors from platelets without clotting. Further, the amount of PDGF released in the PRP sample exposed to electric pulses is comparable to the amount of PDGF released in the PRP sample activated with bovine thrombin. As noted above, no clotting occurs in the PRP sample exposed to electric pulses.

Figure 7:
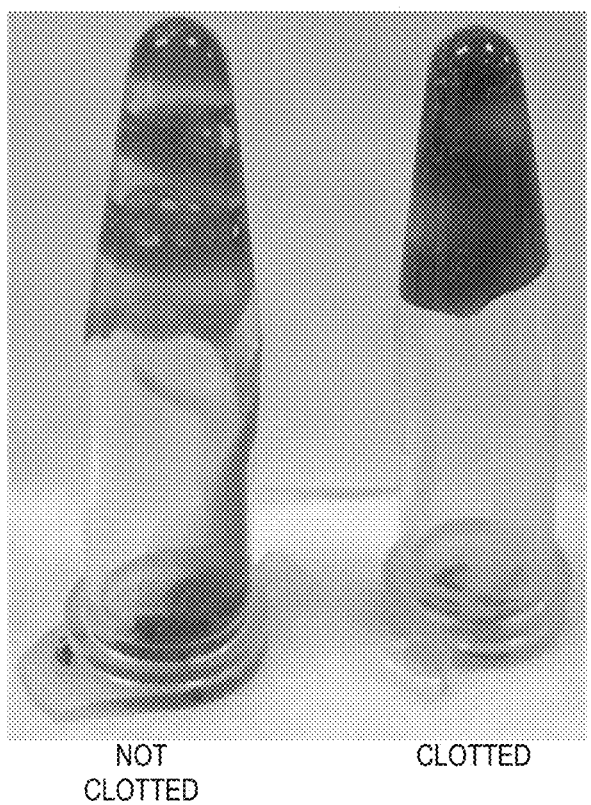
FIG. 7 depicts two samples of platelet rich plasma exposed to pulsed electric fields, as discussed with respect to certain embodiments.

Platelet Rich Plasma Samples with and without Calcium Chloride Addition Prior to Electrical Stimulation Two samples of 3.7× concentration of PRP were exposed to electric pulses. The resulting sample tubes are shown in FIG. 7. In particular, FIG. 7 depicts two samples of platelet rich plasma exposed to pulsed electric fields (under the same electrical conditions). The sample on the right was fully activated with clotting, as demonstrated by the PRP not flowing to the bottom of the tube, and growth factor release. The sample on the left did not clot, as shown by the PRP flowing to the bottom of the tube; however, growth factor release still occurred, as exemplified by the data in FIG. 8 (discussed below).

Calcium chloride was added to the PRP sample in the tube on the right prior to electrical stimulation, but not to the sample on the left. That is, the sample on the right was treated in accordance with method 40 of FIG. 2, while the sample on the left was treated in accordance with the method 60 of FIG. 3. As illustrated, the sample in the tube on the right side is clotted and remains at the tip of the tube, even when inverted. Conversely, the sample on the left has not clotted and flows downward relative to the tip of the tube when inverted.

FIG. 8 depicts a chart comparing the amount of platelet derived growth factor (PDGF) released for PRP samples not exposed to electric pulses, PRP samples exposed to pulsed electric fields without calcium chloride, and PRP samples exposed to pulsed electric fields in the presence of calcium chloride. Clotting occurs in the PRP sample containing calcium chloride, but does not occur in the PRP sample without calcium chloride and exposed to electric pulses. In particular, FIG. 8 is a graph showing the amount of platelet derived growth factor (PDGF) released in the platelet rich plasma samples illustrated in FIG. 7 using various approaches, including approaches discussed herein. This graph shows that growth factor can be released with or without clotting. The amount of PDGF released in the PRP sample without calcium chloride is comparable to the amount of PDGF released in the PRP sample with calcium chloride. Further, no clotting occurs in the PRP sample without calcium chloride.

One or more of the disclosed embodiments, alone or in combination, may provide one or more technical effects useful for medical techniques for ex vivo platelet activation and growth factor release. The present technique for ex vivo platelet activation uses electric stimulation to release growth factors, such as platelet derived growth factors. Certain embodiments may allow operators to extract growth factors from platelets without inducing clotting. Further, the present techniques for ex vivo growth factor release may be performed in part using medical equipment already present in many medical laboratories. The technical effects and technical problems described in the specification are provided as examples only and are not intended to be limiting. It should be noted that the embodiments described in the specification may have other technical effects and can solve other technical problems.

While only certain features of the invention have been illustrated and described herein, many modifications and changes will occur to those skilled in the art. It is, therefore, to be understood that the appended claims are intended to cover all such modifications and changes as fall within the true spirit of the invention. Some of the embodiments can be used for in vivo platelet activation workflows. One could trigger growth factor release in PRP by electrical stimulation, without clotting, and inject this PRP at the site of the injury. The growth factors thus released can be used for wound healing at the site of the injury. Further, in certain embodiments, platelets can be also fully activated by the collagen within the connective tissue.

The invention claimed is:

1. A method for releasing growth factors in blood samples, comprising:
    exposing a blood sample to a sensing signal generated by a sensing circuit;
    estimating, in processing circuitry coupled to the sensing circuit, one or more electrical properties of the blood sample based on the sensing signal;
    parameterizing, in the processing circuitry, based on the one or more electrical properties, a sequence of one or more electric pulses to be applied to the blood sample; and
    exposing the blood sample to the sequence of one or more electric pulses to trigger release of a growth factor in the blood sample, wherein the growth factor release is not accompanied by clotting within the blood sample.

2. The method of claim 1, further comprising:
    collecting the growth factor; and
    treating a patient with the growth factor, wherein the blood sample was acquired from the patient.

3. The method of claim 1, wherein calcium chloride ($CaCl_2$) is not added to the blood sample prior to exposing the blood sample to the sequence of one or more electric pulses.

4. The method of claim 3, wherein the method further comprises adding an ADP blocking agent to the blood sample prior to exposing the blood sample to the sequence of one or more electric pulses.

5. The method of claim 4, wherein the ADP blocking chemical comprises apyrase.

6. The method of claim 1, wherein the one or more electric pulses have an electric field strength between about 0.1 kV/cm and about 350 kV/cm.

7. The method of claim 1, wherein the one or more electric pulses have pulse durations between about 1 nanosecond and about 100 microseconds.

8. The method of claim 1, wherein the growth factor comprises platelet derived growth factor.

9. The method of claim 1, wherein the blood sample is a whole blood sample or a platelet rich plasma.

10. The method of claim 1, wherein the sensing signal comprises a first electric field strength that is smaller than any electric field strength pulse of the one or more electric field pulses.

11. The method of claim 1, wherein the one or more electrical properties comprise a permittivity or a conductivity of the blood sample.

* * * * *

UNITED STATES PATENT AND TRADEMARK OFFICE
CERTIFICATE OF CORRECTION

PATENT NO. : 10,383,915 B2
APPLICATION NO. : 15/251990
DATED : August 20, 2019
INVENTOR(S) : Vasile Bogdan Neculaes et al.

It is certified that error appears in the above-identified patent and that said Letters Patent is hereby corrected as shown below:

On the Title Page

Item (72) Inventors, should read:
(72) Inventors: Vasile Bogdan Neculaes, Niskayuna, NY ( US ); Andrew Soliz Torres, Niskayuna, NY ( US ); Antonio Caiafa, Albany, NY ( US ); Brian Duh-Lan Lee, Rexford, NY ( US ); Allen Lawrence Garner, West Layfayette, IN ( US )

Signed and Sealed this
Seventh Day of March, 2023

Katherine Kelly Vidal
*Director of the United States Patent and Trademark Office*